United States Patent
Carlsson et al.

(10) Patent No.: US 10,206,606 B2
(45) Date of Patent: Feb. 19, 2019

(54) COIL ARRANGEMENT

(71) Applicant: ELEKTA LTD., Crawley (GB)

(72) Inventors: Per Carlsson, Täby (SE); Kjell Eldered, Saltsjö-Duvnäs (SE); Henrik Alexis, Vaxholm (SE)

(73) Assignee: ELEKTA LTD., Crawley (GB)

( * ) Notice: Subject to any disclaimer, the term of this patent is extended or adjusted under 35 U.S.C. 154(b) by 0 days.

(21) Appl. No.: 15/484,505

(22) Filed: Apr. 11, 2017

(65) Prior Publication Data

US 2018/0289283 A1    Oct. 11, 2018

(51) Int. Cl.
| A61B 5/05 | (2006.01) |
| --- | --- |
| A61B 5/055 | (2006.01) |
| A61G 13/00 | (2006.01) |
| A61G 13/06 | (2006.01) |
| A61G 7/10 | (2006.01) |
| A61N 5/10 | (2006.01) |
| A61B 5/00 | (2006.01) |
| A61B 6/04 | (2006.01) |

(52) U.S. Cl.
CPC .......... *A61B 5/0555* (2013.01); *A61B 5/0036* (2018.08); *A61G 7/1025* (2013.01); *A61G 7/1042* (2013.01); *A61G 13/0018* (2013.01); *A61G 13/06* (2013.01); *A61N 5/1049* (2013.01); *A61B 6/0442* (2013.01); *A61G 2210/50* (2013.01); *A61N 2005/1055* (2013.01); *A61N 2005/1063* (2013.01)

(58) Field of Classification Search
CPC ..................................................... A61B 5/05
USPC .............................. 5/601, 600; 600/415, 420
See application file for complete search history.

(56) References Cited

U.S. PATENT DOCUMENTS

| 5,066,915 | A | 11/1991 | Omori et al. |
| --- | --- | --- | --- |
| 5,197,474 | A | 3/1993 | Englund et al. |
| 5,808,468 | A * | 9/1998 | Bis ........................ A61B 5/0555 |
| | | | 324/318 |
| 2007/0035301 | A1 | 2/2007 | Nakabayashi et al. |
| 2009/0027053 | A1 | 1/2009 | Decke et al. |

(Continued)

FOREIGN PATENT DOCUMENTS

| DE | 102012206920 A1 | 10/2013 |
| --- | --- | --- |
| EP | 0857458 A1 | 8/1998 |
| WO | WO 2012/143825 A1 | 10/2012 |

OTHER PUBLICATIONS

Extended European Search Report, dated Sep. 12, 2018, for European Application No. 18166728.8.

*Primary Examiner* — Fredrick C Conley
(74) *Attorney, Agent, or Firm* — Birch, Stewart, Kolasch & Birch, LLP (57) ABSTRACT

A system for moving a patient into and from a medical apparatus includes a patient support arranged outside a treatment space of a medical apparatus, a treatment table arranged inside the treatment space in the medical apparatus and a patient bed movable in a longitudinal direction from the patient support to the treatment table and back by activation of a transferring mechanism. The system may further include a coil arrangement including an anterior coil and a support stand, the support stand resting on the patient bed adjacent to longitudinal edges of the patient bed and being slidable along the patient bed in a longitudinal direction when a patient is placed on the bed.

16 Claims, 5 Drawing Sheets

(56) References Cited

U.S. PATENT DOCUMENTS

2014/0031671 A1\* 1/2014 Friman ................ G01R 33/30
  600/415

\* cited by examiner

COIL ARRANGEMENT

TECHNICAL FIELD

The present invention relates to medical devices, and particularly to systems and devices for moving a patient to and from a magnetic resonance imaging system or a combined magnetic resonance imaging and radiotherapy system.

BACKGROUND

In medical non-invasive therapy system in particular radiotherapy systems, such as conventional linear accelerators or MR Linac systems, the patient anatomy being treated or imaged should be aligned with the radiation isocentre as accurate as possible for each and every set up and each treatment fraction. One source of potential inaccuracy in the alignment is the repositioning of the bed on which the patient rests. As many medical systems require the patient to be placed into an enclosed and confined space, hereinafter called treatment bore, the patient must be set up for treatment outside the treatment bore and then transported into the treatment bore for the medical treatment to begin. Therefore, the bed must be movable between these two locations and positionable to a high degree of accuracy as misalignment during set up may entail that the patient will need to be removed from the medical radiotherapy system and realigned before treatment can commence, and thus wasting time and resources.

It is also of very high importance that the patient positioning is as stable as possible during the movement as well during the treatment or imaging. Hence, the position of the bed in treatment bore in the medical radiotherapy system must be very stable. The process of moving the bed from its support outside the medical radiotherapy system into the treatment bore inside the medical radiotherapy system itself requires careful alignment with the treatment table of the system as well as high degree of stability.

Furthermore, it is also important that the process patient set up and of moving the bed from its support outside the medical radiotherapy system into the treatment space inside the medical radiotherapy system is secure for the patient and easy to handle for the medical staff. The risk of patient injuries must be minimized during movement as well as during treatment in order to provide as high patient security as possible and minimize risk for patient movements during treatment.

Moreover, in medical non-invasive therapy systems, in particular in MR Linac systems, it is of very high importance that all material in the treatment bore or treatment volume is known and taken into account in the planning system. As all material will absorb radiation dose, it is important to reduce the material present in the treatment bore as much as possible and it is also important that the positions of material structures are known.

In summary, there is a number of important factors to take into account when designing a movable bed and treatment table for use in medical radiotherapy systems, such as MR Linac systems. It is of particular importance to make sure that the patient, the patient anatomy and the treatment volume is positioned as accurate and stable as possible. The accuracy and stability require a very reliable positioning of the patient on the patient bed and in some applications a very accurate tracking of the patient during treatment. In addition there is a need for providing good quality imaging when tracking the patient. When using magnetic resonance imaging systems for this it is thus important to position the coil in a stable and accurate position while at the same time ensuring a rather good handling of the system during set up and removal of the patient.

SUMMARY OF THE INVENTION

An object of the present invention is to provide a user and patient friendly movable bed and treatment table for use in medical radiotherapy systems, such as MR Linac systems.

Another object is to provide a more efficient method and dose planning module for planning the treatment and for optimizing the treatment planning.

This and other objects are fulfilled by the present invention as defined by the independent claims. Preferred embodiments are defined by the dependent claims.

According to an aspect of the present invention, there is provided a system for moving a patient into and from a medical apparatus, in particular a non-invasive therapy system, comprising a patient support arranged outside a treatment space of a medical apparatus, a treatment table arranged inside the treatment space in the medical apparatus, a patient bed movable in a longitudinal direction from the patient support to the treatment table and back by means of activation of a transferring mechanism, and a coil arrangement including an anterior coil and a support stand, the support stand resting on the patient bed adjacent to longitudinal edges of the patient bed and being slidable along the patient bed in a longitudinal direction.

Non-invasive therapy system may refer to a medical apparatus and include at least a magnetic resonance imaging system or a radiotherapy system or any combination thereof.

In embodiments of the present invention, the support stand is slidable over and at least partially outward of the patient bed along guide tracks arranged adjacent to said longitudinal edges of said patient bed.

For some applications it may be advantageous to slide the support stand with or without the coil arrangement at least partially outward of the patient bed region. This may for example be helpful during positioning of the patient or for cleaning purposes. When the support stand is slid at least partially outward of the patient bed it may still be partially engaged in the guide tracks and thus not fall off. The support stand may extend outward of the patient bed region up to about 60% of its length as measured in the longitudinal direction. In other words, the support stand may be moved outwards of the patient bed so that a patient mattress is completely free of the support stand.

In embodiments of the present invention, the support stand comprises at least one arc-shaped part having a first end part and a second end part resting on the patient bed.

In embodiments of the present invention, each end part of said at least one arch-shaped part is slidable in a corresponding guide track of said patient bed.

In embodiments of the present invention, a first part of the support stand resting on the patient bed is arranged to be lifted from the patient bed.

In embodiments of the present invention, the first end part of the arch-shaped part is releasable arranged in the corresponding guide track so as to allow the first end part to be lifted from the patient bed.

In embodiments of the present invention, a stop device is arranged to prevent a sliding movement of the anterior coil when activated.

In embodiments of the present invention, the guide tracks comprises stop elements preventing the anterior coil from being slid over an edge of the patient bed.

In embodiments of the present invention, at least one arch-shaped part comprises at least one flexible rail element arranged to fit into said guide track and to be moved into and out of said guide track.

In embodiments of the present invention, the flexible rail element comprises at least one protrusion arranged to snap-lock the end part in said corresponding guide rail so as to allow the rail to slide in said guide track at the same time preventing said rail from being removed from said guide track.

In embodiments of the present invention, the system may comprise a stop device comprising a stop device with an adjustable spring element arranged to fit into said flexible rail element, wherein the adjustable spring element can be adjusted in its width via an adjustment element, for example by rotating the adjustable spring element, so that a friction between the spring element and flexible rail element, respectively, and the guide track can be adjusted when the support stand is positioned on or partially in the guide tracks. According to specific embodiments, the adjustable spring element is s-shaped. This s-shaped adjustable spring element allows to ensure an acceptable friction for the temporary fixation of the coil arrangement and its support stand or frame, respectively, on the patient bed. The acceptable friction may result in a specific limit force needed to move the coil arrangement and support stand even though the adjustable spring element is in fixed position. This limit force is needed to ensure that that the system is still safe for the patient when the coil arrangement is fixed or locked in case the patient manages to stick a limb between the coil arrangement and surrounding structure forming the treatment core while the patient bed moves into the treatment core. There is a hazard for jamming or pinching between coil arrangement and its support stand, respectively, and surrounding structures. By providing such a limit force the coil arrangement will move even though it is in a locked of fixed position when a limb or any other object is present in between the coil arrangement and the surrounding structure forming the treatment bore.

In an embodiment the adjustable element may allow to provide a lower friction limit between the spring element and the flexible rail element, respectively, and the guide track that prevents the coil arrangement from moving when the patient accidentally bumps into it.

In an embodiment the adjustable element may allow to provide an upper friction limit between the spring element and the flexible rail element, respectively, and the guide track that allows the coil arrangement to be moved in case the patient panics.

Such lower and/or upper friction limits may be indicated as a scale on the adjustable element and the support stand or other part of the coil arrangement, for different patients and their physical properties.

The support stand of the coil arrangement may be rigid enough to ensure that if the patient unintentionally bumps into the support frame it's still in the correct position on the patient bed.

In another embodiment the at least one of the corresponding rails may be connected to the first end part and the second end part, respectively, in a flexible manner so that the support stand can be rotated about an axis, which is parallel with the longitudinal direction, while the other of the corresponding rails remains engaged in the corresponding guide track.

The above described flexibility between the rails and the first and second end part, respectively, or between the flexible rail elements and the rails may be achieved by choosing a flexible material or by providing some sort of joint in between.

In an embodiment the support stand may be rotated at least about an angle of 60° as measured from a plane defined by the patient bed and a plane defined by the rails of the support stand.

This means that one of the end parts of the support stand can be lifted while the other remains engaged in or on the guide tracks. This may allow to position a rather big patient in a convenient manner.

In an embodiment the coil arrangement may comprise a height adjustment mechanism for adjusting the height of the anterior coil above the patient bed. This may further improve image quality.

BRIEF DESCRIPTION OF THE DRAWINGS

For a better understanding of the present invention, and to show more clearly how it may be carried into effect, reference will now be made, by way of example, to the following drawings, in which.

DESCRIPTION

Figure 1:
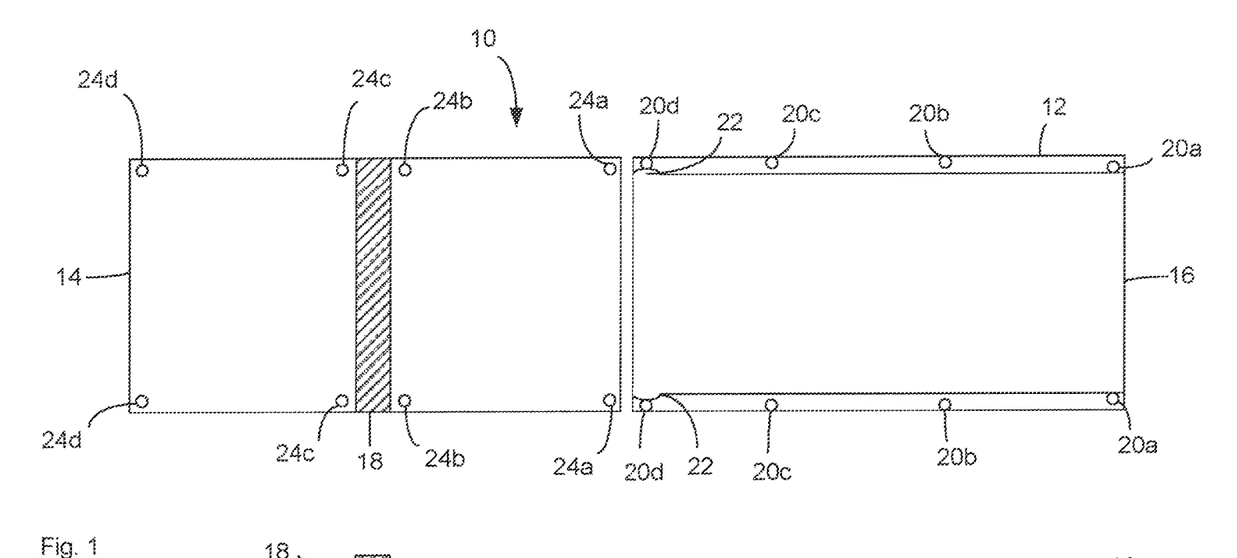
FIG. 1 shows a plan view of a system according to embodiments of the present invention.
Figure 2:
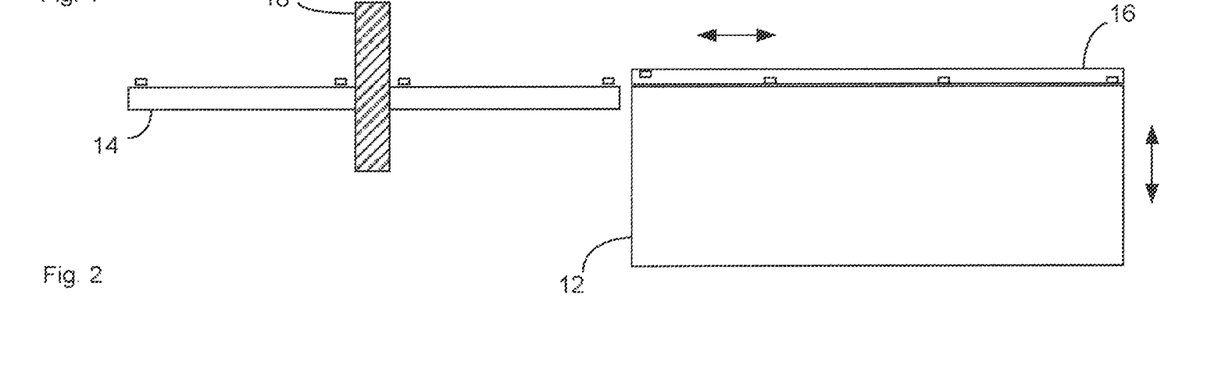
FIG. 2 shows a side view of the system according to embodiments of the present invention.

FIG. 1 shows a plan view of a system 10 according to embodiments of the present invention and FIG. 2 shows a side view of the system of FIG. 1. The system 10 comprises a patient support 12, a treatment table 14, and a bed 16 which is movable between the patient support 12 and the treatment table 14. The treatment table 16 is schematically shown in FIGS. 1 and 2 and may form part of any medical treatment system but is particularly suitable for use in MR Linac radiotherapy systems. Hence, in embodiments of the present invention, the system 10 is arranged at a MR Linac radiotherapy system having radiation heads and radiation sources for generating beams of therapeutic radiation emanating from the radiation heads. One or more collimating elements (e.g. a Multi-leaf collimator in the Linac part) are provided for shaping the beam to conform to a desired cross-section. The radiation heads may be mounted on a rotatable gantry, and controlled to rotate around the patient while directing the radiation towards the axis of rotation and the target within the patient. The target thus receives radiation from multiple angles and a higher dose than the surrounding healthy tissue. The extent of the treatment area 18, i.e. the volume in which the radiation beam operates, is illustrated schematically in FIGS. 1 and 2.

The patient support 12 may comprise a mechanism for altering the height of the support, for example, between a first height and second height. For example, the first (lower) height may be at a level suitable to allow the patient to climb on to the bed 16, while the second (higher) height is a level equal to the height of the treatment table 14 and allows the bed 16 to move between the support 12 and the treatment table 14.

The bed 12 may be moved in a direction along its longitudinal axis between the support 12 and the treatment table 14 in a manner to be described in more detail below. Those skilled in the art will appreciate that any suitable mechanism may be used for moving the bed 16. For example, the bed 16 may be moved by a pulley/belt system, a rack and pinion system, a conveyor belt, etc.

As described above, it is important that the bed can be smoothly transferred or moved between the support 12 and the treatment table 14 so that once on the table 14 the bed is correctly aligned within the system, which in many radiotherapy systems is crucial. In order to ensure that the bed 16 is correctly aligned during initial set-up and treatment, the system 10 may comprise guide elements 20a, 20b, 20c, 20d, arranged on an upper surface of the support 12. Alternatively, guide tracks may be arranged on an upper surface of the support 12 and treatment table 14 and corresponding guide rails may be arranged on the patient bed 16 such that the bed 16 can slide seamlessly between the support and the table.

In the illustrated embodiment, the patient support comprises four pairs of guide elements. However, fewer or more guide pairs may be provided without departing from the scope of the invention. The guide pairs may be uniformly spaced, along the edges of the support 12 so as to prevent the bed 16 from moving significantly in the lateral direction (i.e. up and down the page in FIG. 1, or into and out of the page in FIG. 2).

In the embodiment illustrated in FIGS. 1 and 2, the guide elements are rollers which move over the edge of the bed 16 as the bed moved in the direction along its longitudinal axis. However, those skilled in the art will appreciate that any suitable guiding element which provides a low friction surface along which the bed can travel without sticking may be provided as an alternative. Further, guides needs not be identical, and a mix of different guides may be provided in the same system without departing from the scope of the invention.

The treatment table 14 may comprise a plurality of guide elements 24a, 24b, 24c, 24d, on an upper surface of the table, similar to the guide elements on the support 12.

Figure 3:
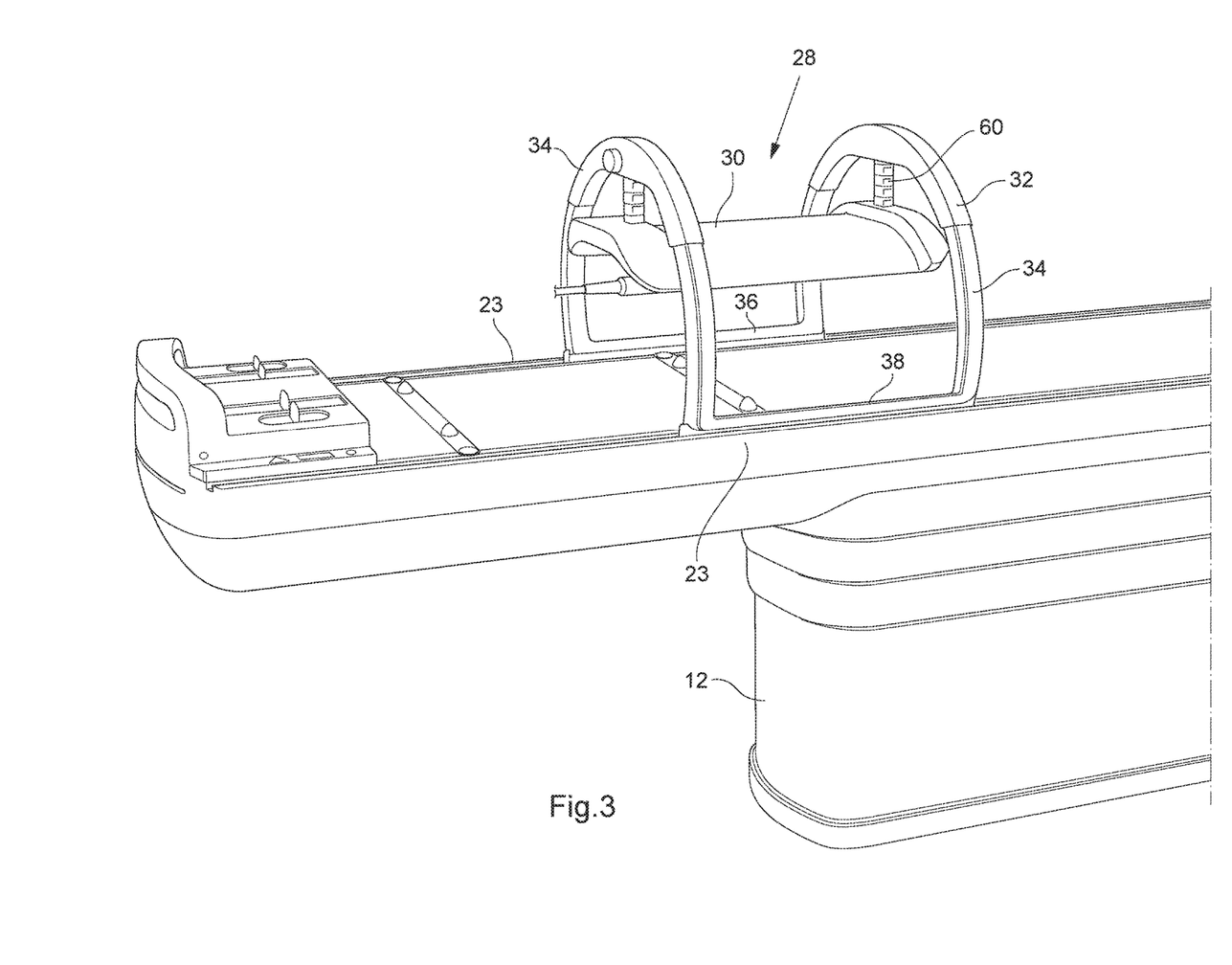
FIG. 3 shows a perspective view of the system according to an embodiment of the present invention.
Figure 4:
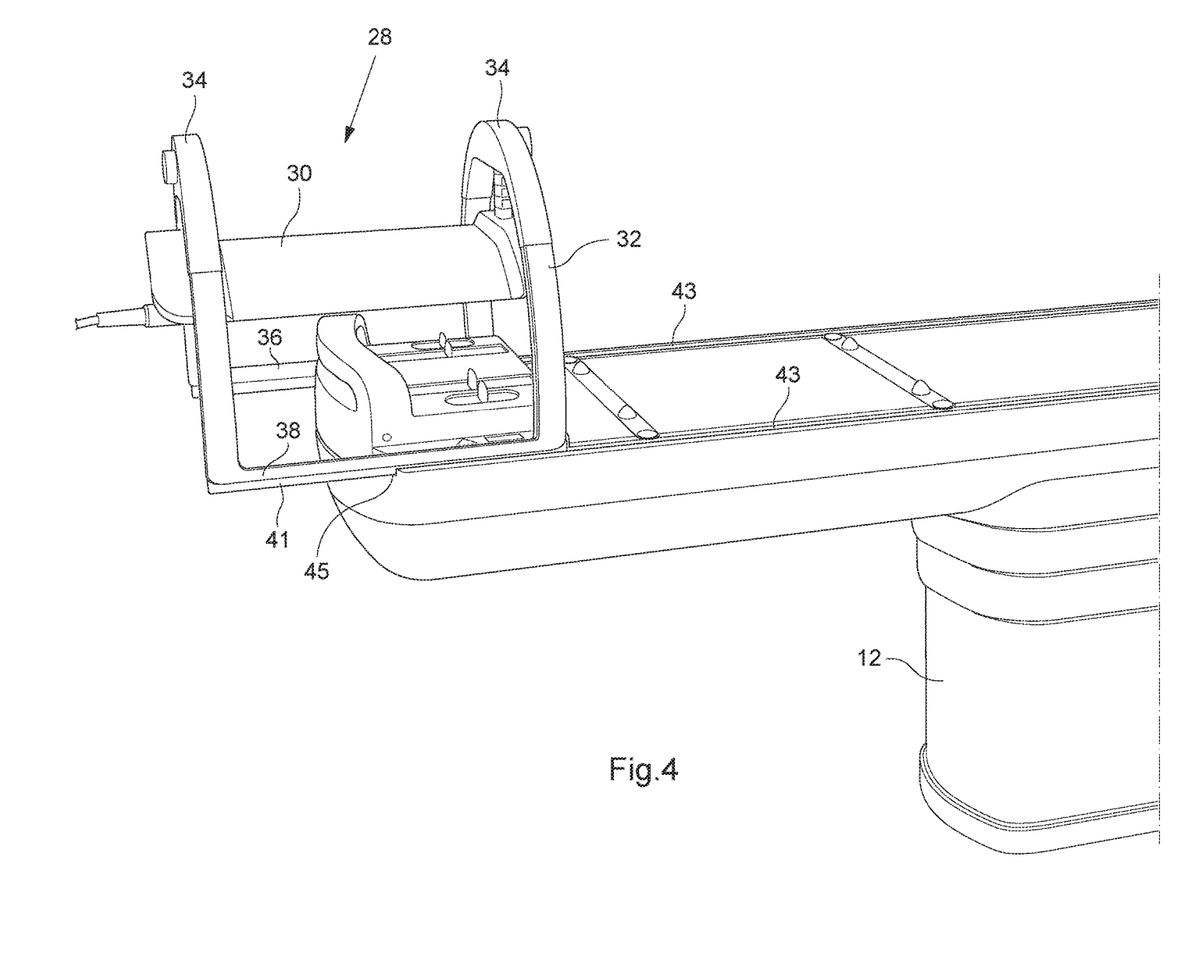
FIG. 4 shows a perspective view of the system according to an embodiment of the present invention.
Figure 5:
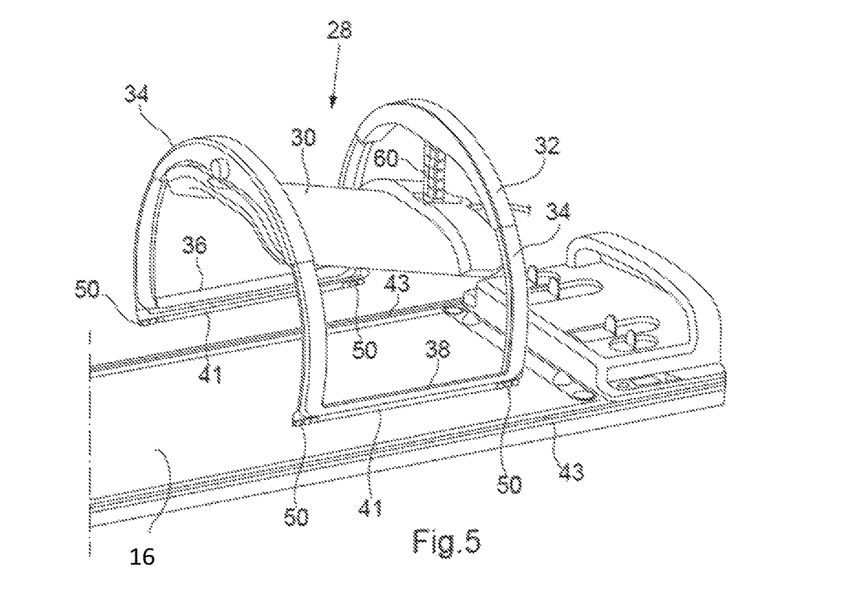
FIG. 5 shows a side view of the system according to embodiments of the present invention.
Figure 6:
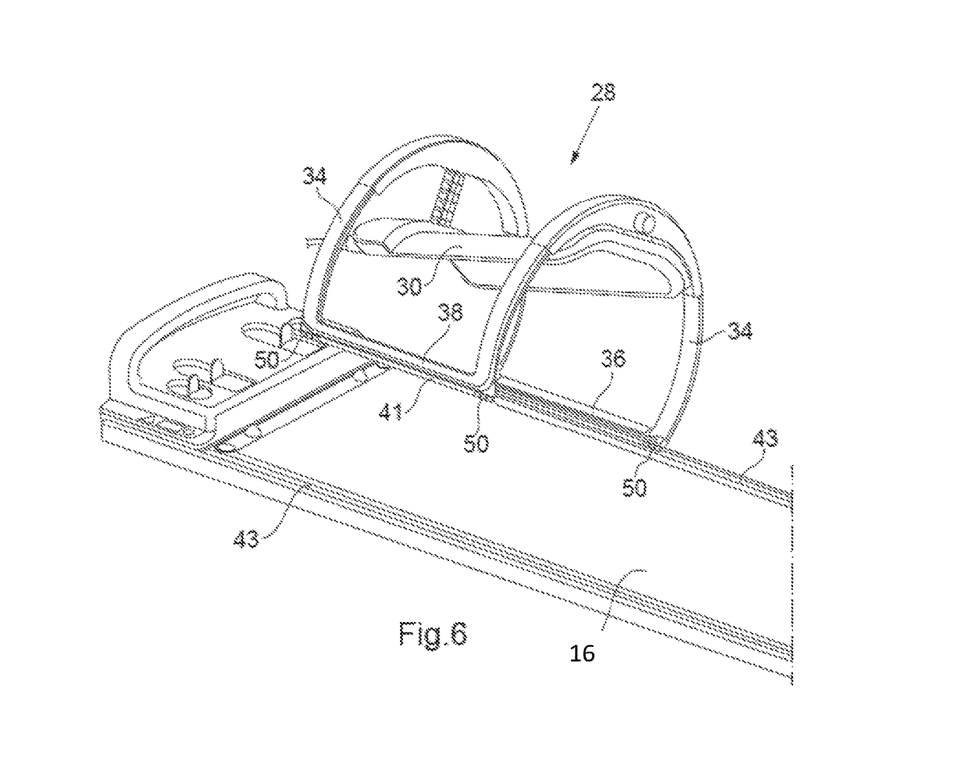
FIG. 6 shows a side view of the system according to embodiments of the present invention.

With reference now to FIGS. 3, 4, 5 and 6, embodiment of the present invention will be described in more detail. A MR coil arrangement 28 including an anterior coil 30 and a support stand 32 is arranged to be slidable along the patient bed 16 in a longitudinal direction when a patient is placed on the bed 16. The support stand 32 rests on the patient bed 16 and is arranged adjacent to longitudinal edges 23 of the patient bed 16 and include rails 41 being arranged to be slidable in grooves or guide tracks 43 provided in the patient bed 16. The coil arrangement 28 may further comprise a height adjustment mechanism 60 for adjusting the height of the anterior coil 30 above the patient bed 16. The height adjustment mechanism 60 may enable an operator to adjust the height of the anterior coil 16 parallel to a plane defined by the patient bed 16 as indicated in FIG. 3 or it may enable an operator to adjust the anterior coil 16 in an oblique manner as seen in relation to the plane defined by the patient bed 16, as shown in FIGS. 5 and 6.

FIG. 4 further illustrates well how the support stand 32 is slid at least partially outward of the patient bed 16. In particular it is slid outwards and away from a patient mattress region so that the patient can easily positioned on the mattress and patient bed 16, respectively. While the support stand 32 is slid partially outwards of the patient bed 16 it may still be partially engaged in the guide tracks 43 and thus not fall off.

Figure 7:
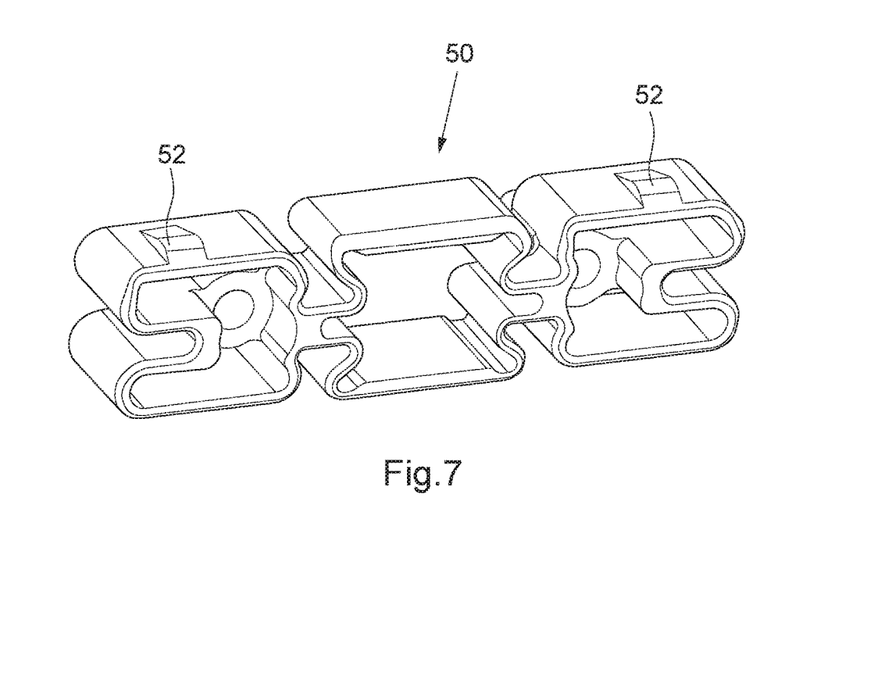
FIG. 7 shows a perspective view of a rail element according to an embodiment of the present invention.

The support stand 32 comprises at least one arc-shaped part 34 having a first end part 36 and a second end part 38 resting on the patient bed 16. Each end part 36, 38 of the at least one arch-shaped part 34 is slidable by means of the rails 41 in a corresponding guide track 43 of the patient bed 16. Further, the end parts 36, 38, both or only one of them, are arranged to be lifted from the patient bed 16, as shown in FIGS. 5 and 6. The first and/or second end part 36, 38 of the arch-shaped part 34 is thus releasable arranged in the corresponding guide track 43 so as to allow the first and/or second end part 36, 38 to be lifted from the patient bed 16, as shown in FIGS. 5 and 6. According to embodiments of the present invention, at least one arch-shaped part 34 or the rail 41 comprises at least one flexible rail element 50 arranged to fit into said guide track 43 and to be moved into and out of said guide track 43. In the shown embodiment, each rail 41 or end part 36, 38 comprises two flexible rail elements 50. Each flexible rail element 50 comprises at least one protrusion 52 arranged to releasably snap-lock the end part 34, 36 in said corresponding guide rail 43 so as to allow the rail 41 to slide in the guide track 43 at the same time preventing the rail 41 from being removed from said guide track 43. In embodiments of the present invention, each flexible rail element 50 comprises four protrusions 52, as shown in FIG. 7.

Figure 8:
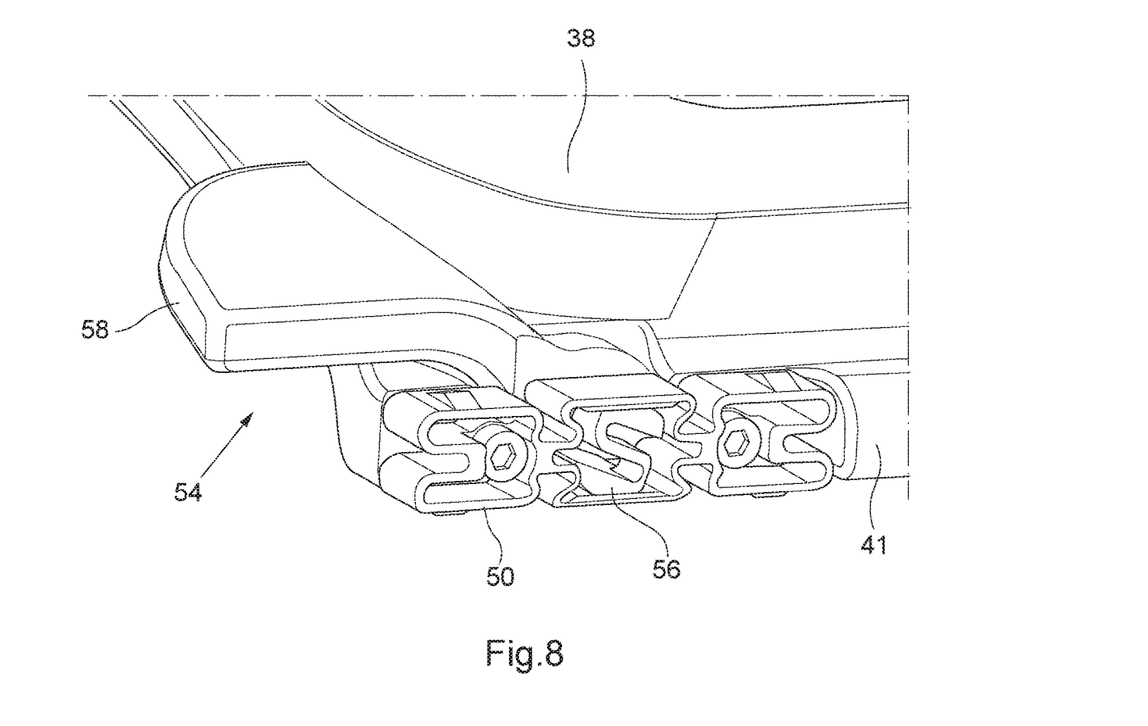
FIG. 8 shows a perspective view of the rail element and a spring element according to an embodiment of the present invention.

Further, with reference to FIG. 8, in embodiments of the present invention, a stop device 54 comprising an adjustable spring element 56 is arranged to fit into the flexible rail element 50, wherein the adjustable spring element 56 can be adjusted to adjust a width of the flexible rail element 50 via an adjustment element 58. In the illustrated embodiment, the adjustable spring element 56 is s-shaped. Thus, the spring element 56 will expand the width of the rail element 50 when turned and thereby make a sliding movement of the coil arrangement 28 slower, hence, it requires more power to slide the coil arrangement 28 along the patient bed 16. That setting is specifically useful when the coil arrangement 28 is in its right position and you don't want the patient to accidentally move the coil out of its position. An incident that could happen if the patient for example starts moving his arms. The spring element 56, or as in the illustrated embodiment the S-shaped element, acts as a spring that alters the spring constant of the flexible rail element 56 when adjusting the adjustment element 58.

The invention claimed is:

1. A system for moving a patient into and from a medical apparatus, comprising:
   a patient support arranged outside a treatment space of a medical apparatus;
   a treatment table arranged inside the treatment space in the medical apparatus;
   a patient bed movable in a longitudinal direction from the patient support to the treatment table and back by activation of a transferring mechanism; and
   a coil arrangement including an anterior coil and a support stand, the support stand resting on the patient bed adjacent to longitudinal edges of said patient bed and being slidable along the patient bed in a longitudinal direction, wherein the anterior coil is fixable with respect to the patient bed and movable together with the patient bed, wherein the support stand comprises at least one arc-shaped part having a first end part and a second end part resting on the patient bed, and wherein said end parts comprise a rail being slidable in a corresponding guide track of said patient bed.

2. The system according to claim 1, wherein the support stand is slidable over and at least partially outward of the patient bed along guide tracks arranged adjacent to said longitudinal edges of said patient bed.

3. The system according to claim 2, wherein the support stand comprises at least one arc-shaped part having a first end part and a second end part resting on the patient bed, wherein said end parts comprise a rail being slidable in a corresponding guide track of said patient bed.

4. The system according to claim 1, wherein an end part of said at least one arch-shaped part comprises at least one flexible rail element arranged to fit into said guide track and to be moved into and out of said guide track.

5. The system according to claim 4, wherein said flexible rail element comprises at least one protrusion arranged to releasably snap-lock said end part-in said corresponding guide rail so as to allow the rail to slide in said guide track at the same time preventing said rail from being removed from said guide track.

6. The system according to claim 4, comprising a stop device with an adjustable spring element arranged to fit into said flexible rail element, wherein the adjustable spring element can be adjusted in its width via an adjustment element so that a friction between the spring element and flexible rail element, respectively, and the guide track can be adjusted when the support stand is positioned on the guide track.

7. The system according to claim 6, wherein the adjustable element allows to provide a lower friction limit between the spring element and the flexible rail element, respectively, and the guide track that prevents the coil arrangement from moving when the patient accidentally bumps into it.

8. The system according to claim 7, wherein the adjustable element allows to provide an upper friction limit between the spring element and the flexible rail element, respectively, and the guide track that allows the coil arrangement to be moved in case the patient panics.

9. The system according to claim 6, wherein the adjustable spring element is s-shaped.

10. The system according to claim 6, wherein the adjustable element allows to provide an upper friction limit between the spring element and the flexible rail element, respectively, and the guide track that allows the coil arrangement to be moved in case the patient panics.

11. The system according to claim 4, wherein the flexible rail element allows to rotate the support stand about an axis, which is parallel with the longitudinal direction, while the other of the corresponding rails remains engaged in the corresponding guide track.

12. The system according to claim 4, wherein at least one of the corresponding rails is connected to the first end part and the second end part, respectively, in a flexible manner so that the support stand can be rotated about an axis, which is parallel with the longitudinal direction, while the other of the corresponding rails remains engaged in the corresponding guide track.

13. The system according to claim 1, wherein the coil arrangement comprises a height adjustment mechanism for adjusting the height of the anterior coil above the patient bed.

14. The system according to claim 1, wherein the support stand can be rotated at least about an angle of 60° as measured from a plane defined by the patient bed and a plane defined by rails of the support stand.

15. The system according to claim 1, wherein at least one of the corresponding rails is connected to the first end part and the second end part, respectively, in a flexible manner so that the support stand can be rotated about an axis, which is parallel with the longitudinal direction, while the other of the corresponding rails remains engaged in the corresponding guide track.

16. A system for moving a patient into and from a medical apparatus, comprising:
 a patient support arranged outside a treatment space of a medical apparatus;
 a treatment table arranged inside the treatment space in the medical apparatus;
 a patient bed movable in a longitudinal direction from the patient support to the treatment table and back by means of activation of a transferring mechanism; and
 a coil arrangement including an anterior coil and a support stand, the support stand resting on the patient bed adjacent to longitudinal edges of said patient bed and being slidable along the patient bed in a longitudinal direction,
 wherein the support stand comprises at least one arc-shaped part having a first end part and a second end part resting on the patient bed, and said end parts comprises a rail being slidable in a corresponding guide track of said patient bed.

\* \* \* \* \*